United States Patent

Jewett

(10) Patent No.: US 6,514,267 B2
(45) Date of Patent: Feb. 4, 2003

(54) ULTRASONIC SCALPEL

(75) Inventor: Warren R. Jewett, Cary, NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 0 days.

(21) Appl. No.: 09/817,633

(22) Filed: Mar. 26, 2001

(65) Prior Publication Data

US 2002/0138090 A1 Sep. 26, 2002

(51) Int. Cl.[7] .............................................. A61B 17/32
(52) U.S. Cl. ........................................................ 606/169
(58) Field of Search ................................ 606/169, 171; 604/22

(56) References Cited

U.S. PATENT DOCUMENTS

| | | | |
|---|---|---|---|
| 2,714,890 A | | 8/1955 | Vang |
| 2,845,072 A | | 7/1958 | Shafer |
| 3,086,288 A | | 4/1963 | Balamuth et al. |
| 3,088,004 A | | 4/1963 | Mueller |
| 3,526,219 A | | 9/1970 | Balamuth |
| 3,636,943 A | * | 1/1972 | Balamuth ................. 156/73.3 |
| 3,651,811 A | | 3/1972 | Hildebrandt et al. |
| 3,888,004 A | * | 6/1975 | Coleman .................. 30/277.4 |
| 3,990,452 A | | 11/1976 | Murry et al. |
| 4,063,557 A | | 12/1977 | Wuchinich et al. |
| 4,188,952 A | * | 2/1980 | Loschilov et al. ............ 30/355 |
| 4,307,720 A | | 12/1981 | Weber, Jr. |
| 4,375,218 A | | 3/1983 | DiGeronimo |
| 4,587,958 A | | 5/1986 | Noguchi et al. |
| 4,823,793 A | | 4/1989 | Angulo et al. |
| 4,832,022 A | | 5/1989 | Tjulkov et al. |
| 4,922,903 A | * | 5/1990 | Welch et al. |
| 4,961,793 A | | 10/1990 | Kubota et al. |
| 5,026,387 A | | 6/1991 | Thomas |
| 5,167,725 A | | 12/1992 | Clark et al. |
| 5,254,082 A | | 10/1993 | Takase |
| 5,263,957 A | | 11/1993 | Davison |
| 5,306,282 A | * | 4/1994 | Muller ....................... 606/167 |
| 5,324,299 A | | 6/1994 | Davison et al. |
| 5,441,512 A | * | 8/1995 | Muller ....................... 606/169 |
| 5,451,220 A | * | 9/1995 | Ciervo ......................... 604/22 |
| 5,897,569 A | * | 4/1999 | Kellogg et al. ......... 310/316.01 |
| 5,948,009 A | * | 9/1999 | Tu ............................. 606/169 |
| 6,080,175 A | | 6/2000 | Hogendijk |
| 2001/0034532 A1 | * | 10/2001 | Cimino ...................... 606/169 |

FOREIGN PATENT DOCUMENTS

JP         05023348 A  *  2/1993   ........... A61B/17/36

OTHER PUBLICATIONS

Web Pages from Innovation regarding Ultracision Harmonic Scalpel.
Web Pages from J&J Gateway regarding Harmonic Scalpel.

* cited by examiner

*Primary Examiner*—Rodney M. Lindsey
(74) *Attorney, Agent, or Firm*—Frommer Lawrence & Haug LLP; Ronald R. Santucci

(57) ABSTRACT

A light, self-contained, hand held, ultrasonic surgical scalpel having a housing, an ultrasonic power source within the housing, to which ultrasonic vibrations are provided to a blade to which result in cutting features by lateral motion as well as by reciprocating motion imparted to the blades with said cutting action being adjustable.

22 Claims, 1 Drawing Sheet

ULTRASONIC SCALPEL

BACKGROUND OF THE INVENTION

1. Field of the Invention

This invention relates to a device for performing surgery particularly an ultrasonic scalpel wherein the scalpel is fully self-contained using batteries as a primary source of power with a switch to permit selection between cutting and cautery modes. When operated the ultrasonic scalpel has the ability for lateral motion as well as reciprocating motion of the scalpel blade causing tissue separation along interstitial margins.

2. Description of the Prior Art

In the prior art, it is well known that an ultrasonic surgery avoids the trauma, extensive scarring, and limitations of thermal cutting of electrosurgery and laser surgery. In ultrasonic surgery, the ultrasonic scalpel takes advantage of dissection technology as a result of oscillating motion of the blades. Ultrasonic energy is transmitted through a connection or mount between the ultrasonic energy source and a hand-held coupler which mounts the surgical tool, for example, a surgical blade mounted at the tip of the coupler. This connection facilitates transmission of ultrasonic motion from the energy source through the coupler to the surgical blade in order to generate vibrations in the blade in a reciprocating motion. This ultrasonic motion is then coupled with the tissue to which the blade is applied.

It was generally thought that the same sharp blades used with hand-held surgical scalpels should also be used with ultrasonic scalpels. It was discovered that in ultrasonic surgical instruments, duller blades achieved exceptional coagulation and cut better than by using sharp conventional scalpel blades. In fact, the duller blade greater transmission of ultrasonic energy is provided to adjoining tissue at the surgical site. This increased transmission was a result of increased blade cutting area in contact with the tissue. Better acoustic coupling as a result of greater transmission of ultrasonic energy enhances cutting capability and capacity for hemostatis. It was found, too, that grinding blades to reduce and modify cross-sectional area enhanced the harmonic "whip" effect.

Existing ultrasonic scalpels can be applied to tissue with a vibrating reciprocating motion. While this reciprocating motion accompanied with dull blades has advantages over ultrasonic scalpels fitted with sharp blades, improved cutting with ease and quality can be achieved if there is lateral motion of the blades as well. Existing ultrasonic scalpels do not have the ability to achieve both ultrasonic lateral and reciprocating motion of the blade.

Existing ultrasonic scalpels also have the disadvantage of relying on external power supplies which connect to the surgical device by cord. Connection by cord to a power source can hamper portability of the scalpel as well as being cumbersome in some surgical operations.

Examples of prior art in this field include U.S. Pat. No. 4,587,958 entitled "Ultrasonic Surgical Device" issued to Noguchi et al. on May 13, 1986; U.S. Pat. No. 4,832,022 entitled "Cryogenic Ultrasonic Scalpel" issued to Tjulkov et al. on May 23, 1989; U.S. Pat. No. 5,026,387 entitled "Method and Apparatus For Ultrasonic Surgical Cutting and Hemostatis" issued to Thomas on Jun. 25, 1991; U.S. Pat. No. 5,167,725 entitled "Titanium Alloy Blade Coupler Coated With Nickel-Chrome For Ultrasonic Scalpel" issued to Clark et al. on Dec. 01, 1992; U.S. Pat. No. 5,254,082 entitled "Ultrasonic Surgical Scalpel" issued to Takase on Oct. 19, 1993; U.S. Pat. No. 5,263,957 entitled "Ultrasonic Scalpel Blade and Methods of Application" issued to Davison on Nov. 23, 1993; U.S. Pat. No. 5,324,299 entitled "Ultrasonic Scalpel Blade and Methods of Application" issued to Davison et al. on Jun. 28, 1994; and U.S. Pat. No. 6,080,175 entitled "Surgical Cutting Instrument and Method of Use" issued to Hogendijk on Jun. 27, 2000.

SUMMARY OF THE INVENTION

It is therefore an object of the invention to provide an ultrasonic scalpel which imparts lateral harmonic motion to the blade and in addition reciprocating motion.

It is therefore a further object of the invention to provide an ultrasonic scalpel which can be used in improved cutting and dissection with ease and quality.

It is therefore a still further object of the invention to provide an ultrasonic scalpel which can be used in incising with superior subsequent wound healing and with minimization of scar tissue.

It is therefore a still further object of the invention to provide an ultrasonic scalpel which can effectively cauterize an incision with minimization of scar tissue.

It is therefore a still further object of the invention to provide an ultrasonic scalpel in a light, self-contained, hand held device thereby improving utility by weight and size advantages.

It is therefore a still further object of the invention to provide an ultrasonic scalpel which is disposable.

To attain the objects described, there is provided an ultrasonic scalpel ideally suited for minimally invasive surgery comprising a housing with a keyed cylinder and a blade coupler having a blade body and a shank extending from the blade body for coupling with a source of ultrasonic energy and transmitting the energy to the blade body. A transducer transmits ultrasonic energy to the blade causing both reciprocating and harmonic lateral motion of the blade. The ultrasonic energy transmitted from the transducer which causes harmonic lateral motion of the blade is due to an offset of approximately one half to two degrees between the drive of the transducer and the armature within the keyed cylinder. In addition the blade may also be subject to reciprocating motion.

The lateral harmonic motion produced is the reason for the ease and quality of a surgical cut and is the preferred embodiment of this invention. Improved cutting by enhanced tissue separation along interstitial margins is demonstrated. In the coagulation mode, the scalpel can operate at lower frequency and higher power providing thermal sealing. The proteinatious nature of tissue breakdown in the region surgerized at cutting frequency causes development of adherent surfaces leading to a coagulation effect. This coagulation effect enhances healing with a minimization of scar tissue.

The ultrasonic scalpel of this invention does not require the use of a power cord connected to an external source. A power cord in the close area of surgical operations can be cumbersome and hinder ease of movement of the ultrasonic scalpel. Instead, the power source of the scalpel is batteries in a section of the ultrasonic scalpel housing itself; however, there is capability for an external power source if needed. Also, the weight and size of other required parts of the ultrasonic scalpel such as the electrical actuator and the circuit components with transformer can be reduced. Since the entire ultrasonic scalpel could operate without a separate power supply, the unit is conceivable disposable.

These and other objects and characteristics of the present invention will become apparent from the further disclosure to be made in the detailed description given below.

BRIEF DESCRIPTION OF THE DRAWINGS

The preferred embodiments of the present invention will now be explained in detail with reference to the accompanying drawings, wherein.

DETAILED DESCRIPTION OF THE PREFERRED EMBODIMENT

Figure 1:
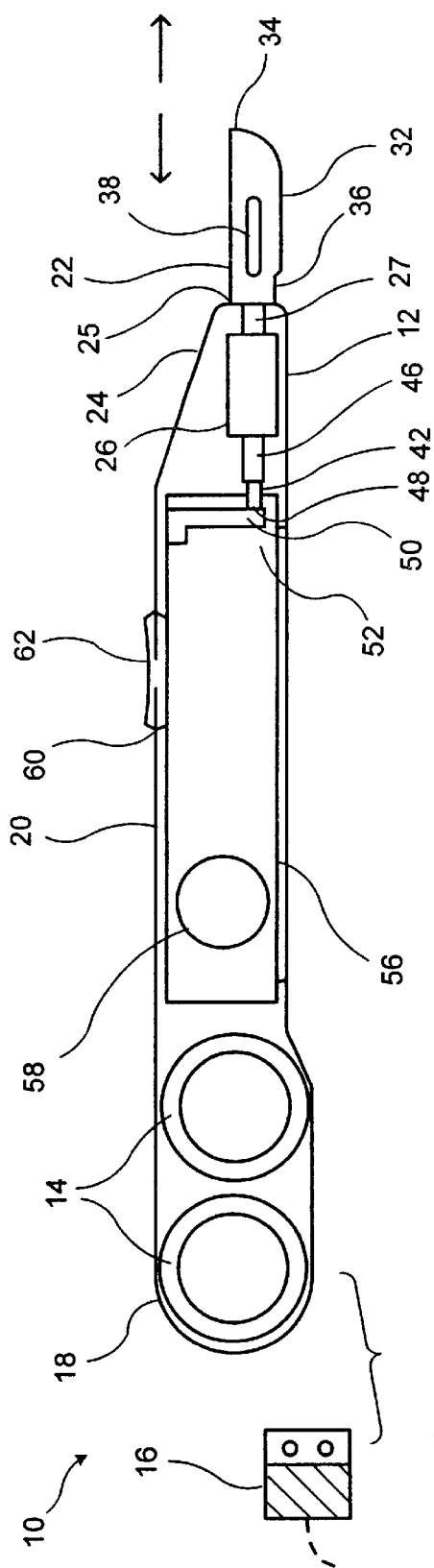
FIG. 1 is a side view in section of the ultrasonic scalpel of the present invention.

Referring now to the drawings in detail wherein like numerals refer to like elements throughout the several views, FIG. 1 is a side cut-away view of ultrasonic scalpel 10.

Housing 12 of the ultrasonic scalpel 10 of FIG. 1 is shaped to be grasped by the surgeon to allow the surgeon to grip and manipulate during surgery. The shape of housing 12 is an elongated rounded body with varying circumferences. At the far end of the body of housing 12, removable sections are located on the housing face to allow for the insertion of a power source, batteries 14 and a power cord 16. From the power end 18, the circumference of the body decreases to a gripping area 20 which is the majority of the outside surface area of the housing 12. From the gripping area 20, the circumference of the body decreases to a circumference slightly larger than the width of blade 22, which allows improved sight of the action of blade 22. At the distal end 24 of the body of housing 12, an aperture 25 is provided for insertion of blade 22 to connect with the keyed cylinder 26 of the ultrasonic scalpel 10.

Figure 2:
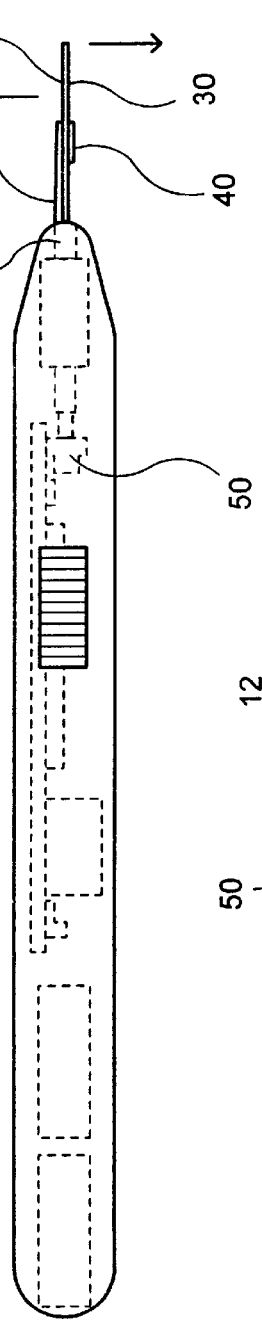
FIG. 2 is a top plan view showing the scalpel of FIG. 1.

In FIG. 2, blade 22 can be one of several special purpose blades pre-fitted for the ultrasonic scalpel for different types of surgery or designed for reciprocating and/or lateral motion of the ultrasonic scalpel. Blade 22 has opposite side faces 28 and 30 and may be made of metal, ceramic, a combination of both or other material suitable for the purpose. For example, when an ultrasonic scalpel is made for lateral motion only, specially shaped and ground blades ensure proper mass and balance throughout the length of the blade.

In FIG. 1 blade 22 has a side edge 32 and a tip 34 opposite the shank 36. An aperture 38 is provided in the shank face for receiving the extrusion 27 of keyed cylinder 26. As shown in FIG. 2, extrusion 27 has a flattened section with a raised surface 40 on one side face sized to fit conformably with the aperture 38 of blade 22.

As shown in FIG. 1, blade 22 moves in relation to the movement of armature 42 in a reciprocating motion as depicted by the direction arrows. Reciprocating motion is vibration in the direction of the axis of the blade 22. FIG. 2 depicts the motion of blade 22 in relation to the movement of armature 42 in a lateral motion as depicted by the direction arrows. Lateral motion is vibration in a direction perpendicular to the axis of the blade 22.

It should be understood that in certain circumstances lateral motion alone may be sufficient and desirable without reciprocating motion. Without reciprocating motion imparted to scalpel blade 22, tissue separation occurs only at the nodes of harmonic motion and sugerization occurs as the scalpel blade is manually drawn across the surgical field. The blade 22 and driver 50 assembly may be fabricated in a manner to provide only lateral "whip" motion along the length of blade 22.

Figure 3:
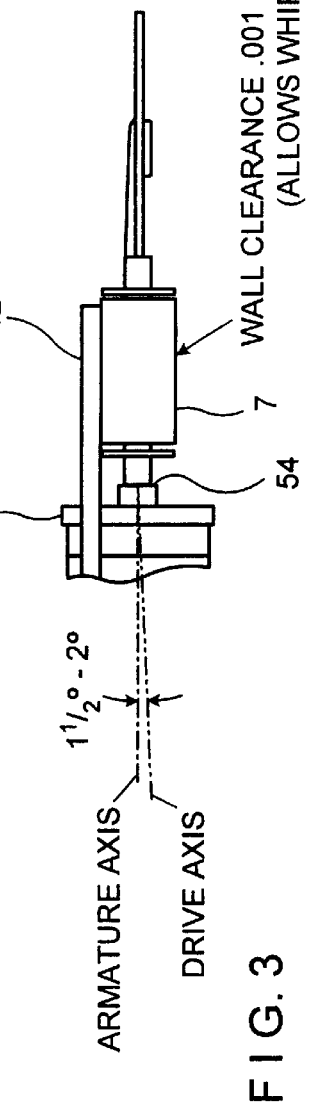
FIG. 3 is a top plan view of the cylinder/armature arrangement of the present invention illustrating the degree of difference between the armature axis and the drive axis as well as the wall clearance between the keyed cylinder and the housing of the ultrasonic scalpel.

In FIG. 3, the elongated flattened section 44 of extrusion 27 is the blade attachment section. The tubular section 46 of the armature 42 is the keyed cylinder 26 attachment area. Inside the body of the housing 12 near the aperture 25 is the keyed cylinder 26. The interior of the keyed cylinder 26 confines the armature 42 and transmits the ultrasonic vibration of the armature 42 to blade 22.

The armature 42 has a solid tubular section 46 which moves within and impacts the movement of the keyed cylinder 26. The other end 48 of the body of armature 42 slidably inserts into the driver 50 of transducer 52. Armature 42 can slidably insert into the driver 50 at an offset as exaggerated in the illustration of FIG. 3. The driver 50 of the transducer 52 is rounded and has a recessed area 54 for engaging the armature 42.

The ultrasonic scalpel 10 is energized by a tool tip ultrasonic transducer 52. The transducer 52 vibrates and transmits this vibration through the driver 50 and armature 42 at a controlled frequency to the blade 22, causing reciprocating motion of the blade 22. The blade excursion is a function of electrical power input to the transducer 52.

Ultrasonic vibration for lateral harmonic motion of blade 22 is caused by the one half to two degree offset of the driver 50 axis and the armature 42 axis. The keyed cylinder 26 has a one-thousandth of an inch (0.001") clearance from the housing 12 to allow whip movement caused by the lateral harmonic motion. The ultrasonic scalpel 10 can be limited to transmitting ultrasonic vibration for solely lateral harmonic motion.

In FIG. 3, a piezo beam driver electrically connected to circuit board 56 could provide lateral "whip" motion when connected directly to blade 22. An anchor section of driver 50 is the blade attachment section. The driver is preferably a Thunder Beam of Thunder Technology described with transducer 52; however suitable alternatives may be used.

The transducer 52 of FIG. 1 has a piezoelectric driver which preferably contains Thunder Technology, which is a high deformation Piezo electrical actuator, (described and illustrated in U.S. Pat. No. 5,632,841 issued May 27, 1997 to NASA; U.S. Pat. No. 5,639,850 issued Jun. 27, 1997 to NASA; and U.S. Pat. No. 6,030,480 issued Feb. 29, 2000 to Face International, the disclosures of which are incorporated herein by reference); however, those skilled in the art will recognize various equivalent substitutions. Operating frequencies of between 40 kHz and 65 kHz have been found to work particularly well. High voltage to the transducer 52 is provided by way of the circuit board 56. The circuit board 56 is a wafer-type rectangular shape. At one end of its face, the circuit board 56 connects electrically to the transducer 52.

To provide high voltage to the circuit board 56, a transformer 58 will be connected electrically on the circuit board face of the end opposite the attached transducer 52. The transformer 58 will preferably be a Transoner type (described and illustrated in U.S. Pat. No. 5,834,882 issued to Face International, the disclosure of which is incorporated herein by reference). Transoner is a multi-layer piezo electric transformer. Of extremely small size, this device can step up 6 volts to as high as 900 volts; however, those skilled in the art will recognize various equivalent substitutions.

To supply power to the transformer 58, the housing 12 provides interior space for two batteries 14 and an aperture 18 for a connection to an external power source 16. These power sources are connected electrically to the transformer 58. The batteries 14 for the power source can have a lithium core which would enable the ultrasonic scalpel 10 to be operated for 15 minutes. This is adequate because in many surgical procedures, the ultrasonic scalpel 10 is not in continuous use.

The housing 12 has an aperture opening 60 on the exterior gripping section 20 of the body for function switch 62. Function switch 62 comfortably fits in the opening 60 of the exterior of the housing 12 and is attached to the circuit board 56. The function switch 62 is in the form of a sliding button. The function switch 62 allows the operator to control the application of ultrasonic vibrations to the blade 22 for cutting and coagulation modes.

Without the need for but with the ability to use an external power supply, the ultrasonic scalpel 10 can be disposable. Also, the ultrasonic scalpel 10 one can be available in different power and frequency models, for varying surgical application.

While the invention has been described in connection with what is considered to be the most practical and preferred embodiment, it should be understood that this invention is not to be limited to the disclosed embodiment, but on the contrary, is intended to cover various modifications and equivalent arrangements included within the spirit and scope of the appended claims.

What is claimed is:

1. An ultrasonic scalpel including:
   a housing having an interior;
   a support piece in said housing;
   a blade coupled to said support piece;
   an armature in said support piece;
   driver means for applying ultrasonic energy to the blade along its axis through said armature and said support piece to vibrate the blade in a lateral harmonic motion.

2. The ultrasonic scalpel of claim 1, wherein said driver means is mounted on said armature and applies energy to said blade along its axis through said armature and said support piece to move the blade in a reciprocating motion.

3. An ultrasonic scalpel including:
   a housing having an interior;
   a support piece in said housing;
   a blade coupled to said support piece;
   driver means for applying ultrasonic energy to the blade along its axis through said support piece to vibrate the blade in a lateral whiplike motion.

4. The ultrasonic scalpel of claim 2 wherein said driver means is mounted at an offset angle on said armature.

5. The ultrasonic scalpel of claim 2 wherein said support piece to move said blade is a keyed cylinder.

6. The ultrasonic scalpel of claim 5 wherein said blade is pre-fitted for said keyed cylinder.

7. The ultrasonic scalpel of claim 2 further including a switch attached to said housing.

8. The ultrasonic scalpel of claim 7 wherein said switch permits selection of cutting and cautery modes.

9. The ultrasonic scalpel of claim 3 further including a switch attached to said housing, wherein said switch activates and de-activates the ultrasonic scalpel.

10. The ultrasonic scalpel of claim 4 wherein the said offset angle is two degrees between the axis of said blade and the axis of said driver.

11. The ultrasonic scalpel of claim 2 or 3 further including a transducer in said housing for transmitting vibration through said driver means and said support piece to said blade.

12. The ultrasonic scalpel of claim 11 wherein said transducer is a high deformation electrical actuator.

13. The ultrasonic scalpel of claim 11 further including a transformer in said housing for voltage to the transducer.

14. The ultrasonic scalpel of claim 13 wherein said transformer is a multi-layer piezo electric transformer.

15. The ultrasonic scalpel of claim 14, wherein said transformer can step up six volts to 900 volts.

16. The ultrasonic scalpel of claim 13 further including a power source for supplying power to said transformer.

17. The ultrasonic scalpel of claim 16, wherein said power source is provided externally.

18. The ultrasonic scalpel of claim 16, wherein said power source is provided by batteries in said housing.

19. The ultrasonic scalpel of claim 18, wherein said batteries comprise lithium.

20. The ultrasonic scalpel of claim 2 or 3, wherein said scalpel can be adjusted to a plurality of frequency settings.

21. The ultrasonic scalpel of claim 2 or 3, wherein said scalpel can be adjusted to a plurality of power modes.

22. The ultrasonic scalpel of claim 2 or 3, wherein said ultrasonic scalpel is disposable.

* * * * *